(12) United States Patent
Turek (10) Patent No.: US 11,166,839 B2
(45) Date of Patent: Nov. 9, 2021

(54) PASSIVE TONGUE RETENTION DEVICE

(71) Applicant: Hibobi Pty Ltd, Killara (AU)

(72) Inventor: Gregory Turek, Killara (AU)

(73) Assignee: HIBOBI PTY LTD, Killara (AU)

( * ) Notice: Subject to any disclaimer, the term of this patent is extended or adjusted under 35 U.S.C. 154(b) by 699 days.

(21) Appl. No.: 15/505,886

(22) PCT Filed: Aug. 21, 2015

(86) PCT No.: PCT/AU2015/050483
§ 371 (c)(1),
(2) Date: Feb. 22, 2017

(87) PCT Pub. No.: WO2016/026008
PCT Pub. Date: Feb. 25, 2016

(65) Prior Publication Data
US 2017/0266033 A1    Sep. 21, 2017

(30) Foreign Application Priority Data

Aug. 22, 2014  (AU) ................................ 2014903320

(51) Int. Cl.
| | | |
|---|---|---|
| *A61F 5/56* | (2006.01) | |
| *A61B 13/00* | (2006.01) | |
| *A61C 5/00* | (2017.01) | |

(52) U.S. Cl.
CPC .............. *A61F 5/566* (2013.01); *A61B 13/00* (2013.01); *A61C 5/007* (2013.01)

(58) Field of Classification Search
CPC . A61F 5/56; A61F 5/566; A61B 13/00; A61B 1/24; A61C 5/007; A61C 5/30;
(Continued)

(56) References Cited

U.S. PATENT DOCUMENTS 1,534,802 A * 4/1925 Fred ..................... A61C 13/225
                                                 433/177
3,023,499 A * 3/1962 Theophilos .......... A61C 13/225
                                                 433/172
(Continued)

FOREIGN PATENT DOCUMENTS

| JP | 2003-275311 A | 9/2003 |
| WO | 2006-063403 A1 | 6/2006 |
| WO | 2016-026008 A1 | 2/2016 |

OTHER PUBLICATIONS

Australian Patent Office, Written Opinion of the International Searching Authority for Application No. PCT/AU2015/050483, dated Oct. 9, 2015.
(Continued)

*Primary Examiner* — Ophelia A Hawthorne
(74) *Attorney, Agent, or Firm* — SoCal IP Law Group LLP; Guy Cumberbatch (57) ABSTRACT

An oral appliance that includes tongue positioning structures which are useful in treating snoring, OSA and related disorders. The invention provides a passive tongue location device which includes cavities located on the internal surface adjacent the tongue, the cavities operatively providing a retentive effect on the tongue when it is in its relaxed state. Further, the present invention provides an oral device adapted to operatively enhance the operation of a sleeping user's airway, including a carrier adapted to be positioned over at least some of the lower teeth of the user and having an interior projection over at least part of the gums of a user, the projection defining a pair of opposed cavities, the cavities being shaped and operatively adapted so that the tongue of the sleeping user will passively engage the cavities.

20 Claims, 8 Drawing Sheets

(58) Field of Classification Search
CPC .. A61C 5/00; A61C 7/00; A61C 13/22; A63B 71/085; A63B 71/08
USPC ....... 128/848, 857, 860, 861, 862, 863, 869; 433/172
See application file for complete search history.

(56) References Cited

U.S. PATENT DOCUMENTS

| | | | | |
|---|---|---|---|---|
| 4,304,227 | A | 12/1981 | Samelson | |
| 4,812,121 | A * | 3/1989 | Winder | A61C 13/24 433/172 |
| 5,052,409 | A * | 10/1991 | Tepper | A61F 5/566 128/859 |
| 5,752,822 | A * | 5/1998 | Robson | A61F 5/566 128/860 |
| 6,129,084 | A * | 10/2000 | Bergersen | A61F 5/566 128/848 |
| 6,837,246 | B1 * | 1/2005 | DeLuke | A61F 5/566 128/860 |
| 7,730,890 | B2 * | 6/2010 | Enoch | A61F 5/566 128/848 |
| 8,485,197 | B2 * | 7/2013 | Metz | A61C 7/08 128/848 |
| 2010/0043804 | A1 * | 2/2010 | Razmovski | A61F 5/566 128/848 |
| 2010/0043805 | A1 * | 2/2010 | Kelly | A61F 5/566 128/848 |
| 2010/0261133 | A1 * | 10/2010 | Lax | A61C 9/0006 433/71 |
| 2012/0138071 | A1 * | 6/2012 | Summer | A61F 5/566 128/860 |
| 2014/0076332 | A1 * | 3/2014 | Luco | A61F 5/566 128/848 |

OTHER PUBLICATIONS

Australian Patent Office, Notification of the Transmittal of the International Search Report and the Written Opinion of the International Searching Authority, or the Declaration for Application No. PCT/AU2015/050483, dated Oct. 9, 2015.

* cited by examiner

PASSIVE TONGUE RETENTION DEVICE

TECHNICAL FIELD

The present invention relates to oral devices for the treatment of obstructive sleep apnoea (OSA), snoring and related disorders.

BACKGROUND OF THE INVENTION

OSA is a chronic condition which affects many sufferers around the world. One treatment which has been applied is the continuous positive air pressure (CPAP) system, in which a mask and associated pump is used to apply positive air pressure to the airway in order to prevent its collapse. Whilst CPAP is effective in many cases, it suffers from an issue of poor on-going compliance from patients.

Another approach has been to use oral appliances of various kinds. Mandibular advancement splint (MAS) devices hold the lower jaw forward, so as to better open the airway, and keep the base of the tongue forward from the airway opening. Holding the lower jawbone forward helps open up the pharyngeal space above the airway, however, in most cases it is the base of the tongue falling back that blocks the pharyngeal airway. Holding the lower jaw forward exerts some forward influence on the resting position of the tongue. However the tongue is only loosely connected to the lower jaw bone, so holding the lower jaw forward does not necessarily hold the tongue far enough forward to prevent airway obstruction.

MAS devices are very well tolerated, however, they have proved most effective in cases of snoring and mild OSA, particularly when patients have relatively low BMI. In more severe OSA and higher BMI patients, MAS devices have proved less effective.

Other devices have been proposed which operate by directly gripping the tongue. For example, US Patent application No. 2009/0126742 by Summer discloses a tongue gripping and restraining device having a surface with relatively sharp protrusions which mechanically squeezes the tongue from both sides. Other tongue control devices are disclosed, for example, in U.S. Pat. No. 5,988,170 to Thomas, and CA2206701 to De Voss. The disclosures of these references are hereby incorporated by reference.

PCT application No. WO 2013/086586 by the present applicant (the prior application) discloses several types of oral appliances which directly address the issue of tongue positioning. This disclosure is hereby incorporated by reference into the present application.

It is an object of the present invention to provide oral appliances including tongue positioning structures which are useful in treating snoring, OSA and related disorders.

SUMMARY OF THE INVENTION

In a first broad form, the present invention provides a passive tongue location device which includes cavities located on the internal surface adjacent the tongue, the cavities operatively providing a retentive effect on the tongue when it is in its relaxed state.

According to one aspect, the present invention provides an oral device adapted to operatively enhance the operation of a sleeping user's airway, including a carrier adapted to be positioned over at least some of the lower teeth of the user and having an interior projection over at least part of the gums of a user, the projection defining a pair of opposed cavities, the cavities being shaped and operatively adapted so that the tongue of the sleeping user will passively engage the cavities.

According to another aspect, the present invention provides a method of forming an oral device adapted to operatively enhance the operation of a sleeping user's airway, the method including the steps of forming a device adapted to be positioned over at least some of the lower teeth of the user, and forming an interior projection over at least part of the gums of a user, the projection defining a pair of opposed cavities, the cavities being shaped and operatively adapted so that the tongue of the sleeping user will passively engage the cavities.

Implementations of the present invention provide advantages in effective positioning of the tongue, so as to maintain an effective airway, while minimising the discomfort and risk of injury for the user.

BRIEF DESCRIPTION OF THE DRAWINGS

Illustrative implementations of the present invention will be described with reference to the accompanying drawings, in which.

DETAILED DESCRIPTION OF THE INVENTION

The present invention will be described with reference to several specific implementations. However, it is important to understand that the present invention may be implemented as an addition to many existing types of oral devices, and that the implementations are not limited in any way to the specific examples disclosed. It is specifically contemplated that in some of the applications the present invention will be combined with structures such as MAS devices, other types of splints and oral devices, and such variations are to be understood as falling within the scope of the disclosure.

It has been recognized by the present inventor that it is critical for the success of any practical device to not only assist in preventing the tongue from moving to an obstructive position during sleep, but also to ensure that the device is both safe and comfortable for the user. No device, however effective, will achieve long term user compliance unless it is well tolerated and provides only a minimum of discomfort for the user. The device must be tolerated for relatively long periods of time, and minimise any disruption to sleep.

In order to better understand the operation of implementations of the present invention, it is important to consider the behaviour of the tongue. The tongue is a difficult organ to retain in a desired position in the mouth because it is very sensitive, slippery and, most importantly, variable in size, shape and mechanical properties. The underside of the tongue is a very delicate mucous membrane, while the upper surface is a much tougher yet still sensitive surface.

The tongue is a muscular organ, with its own complex set of reflexes and autonomous behaviours. It performs many complex tasks without conscious control. Failure to recognise and take account of the complex characteristics of the tongue when designing and implementing oral devices is likely to lead to unsatisfactory outcomes.

One aspect of tongue behaviour which has been newly identified by the inventor is tongue flow adaptability, or TFA. During sleep, the tongue generally becomes softer and smaller, reduces in tone, and in general enters a relaxed state. When the tongue is placed over another surface in this relaxed state, the surface of the tongue flows in a fluid-like way so as to intimately conform its surface to the other, external surface it is in contact with. It will flow over, around and grip or adhere to the surface. It is this TFA feature which provides the surfaces and shapes according to implementations of the present invention with the ability to become enveloped by tongue tissues and thus to tend to hold the corresponding tongue surface, so as to maintain the relaxed tongue in the desired position.

The degree of grip or attachment provided according to implementations of the present invention, which will be further explained below, will not resist a conscious withdrawal of the tongue, and serves only to maintain adequate engagement between the device and the tongue in the event of changes in the size and consistency of the tongue.

Implementations of the present invention do not in any way seek to actively restrain the tongue. Rather, the relaxed tongue naturally and spontaneously interacts with the surfaces provided, and is sufficiently held in place during sleep by the TFA effect. Implementations of the present invention accordingly encourage the tongue, by exploiting its natural behaviour, to remain in a forward position in the mouth and adjacent the lower palate, so as to reduce the likelihood of obstructions of the airway by the tongue. The tongue can at any time be consciously withdrawn.

An important factor for any device seeking to correctly position the tongue is the necessity to allow the tongue to be instantly withdrawn from the device without trauma. The tongue is very powerful and flexible, and attempts to hold it with sufficient force to resist all attempts at withdrawal are virtually impossible, because even if the action results in trauma, one can pull ones tongue out of virtually any entrapment. Sudden events such as sneezing, coughing or yawning require instant reflex tongue withdrawal. Any method of restraining or holding the tongue which does not allow for instant involuntary reflex withdrawal will inevitably result in trauma to the tongue upon sudden withdrawal. Devices using surfaces with angular or protruding gripping elements are likely to traumatize the tongue if it is suddenly withdrawn.

Another aspect of tongue behaviour is the tongue-tongue reflex. When a pressure or touch is applied to the tip and surrounding areas of the tongue, the tongue orients itself towards that stimulus. The stronger the stimulus, the greater the probability that the tongue will move towards the stimulus. Further details regarding tongue reflexes can be obtained from the literature, for example from Moses, 'Dentist's treatment of snoring', Sleep Diagnosis and Therapy, vol 2 no 6 December 2007, the disclosure of which is hereby incorporated by reference.

The present invention is primarily contemplated to be used in association with a custom formed splint device, of the type that dentists routinely take impressions for in relation to other devices. The device may be formed from any suitable material, for example a dental acrylic, for example PMMA. However, the present invention may be implemented using any suitable material, or any suitable fitting process.

It will be appreciated that this implementation lends itself well to CAD manufacture, for example using conventional 3D printing such as is used by Resmed Limited with their Narval device. Alternatively, conventional dental appliance manufacturing techniques and material may be used. It will be appreciated that implementations of the present invention, in which a tongue support structure is integrated into a lower splint, may be developed with most existing oral sleep devices.

As a general point, it has been found important by the inventor in any practical device to ensure that the surfaces to be engaged by the tongue are sufficiently smooth, and avoid sharp edges, sharp curves and projections. The tongue is a highly adaptive organ and is constantly seeking onformation about the objects and surfaces within the mouth. If sharp or abrupt projections are perceived, the tongue will worry at them, thereby reducing the comfort of the device. The tongue may even be injured in this case. This is turn will likely lead to lower levels of user compliance with the use fo the device. This is an issue not only at the general design level, but at the level of each specific device as constructed for a user. If issues such as this are encountered, the device needs to be modified to make it suitable for the comfort of the user. This may require re-shaping, abrasive removal or smoothing or material, or building up of surfaces.

Figure 1:
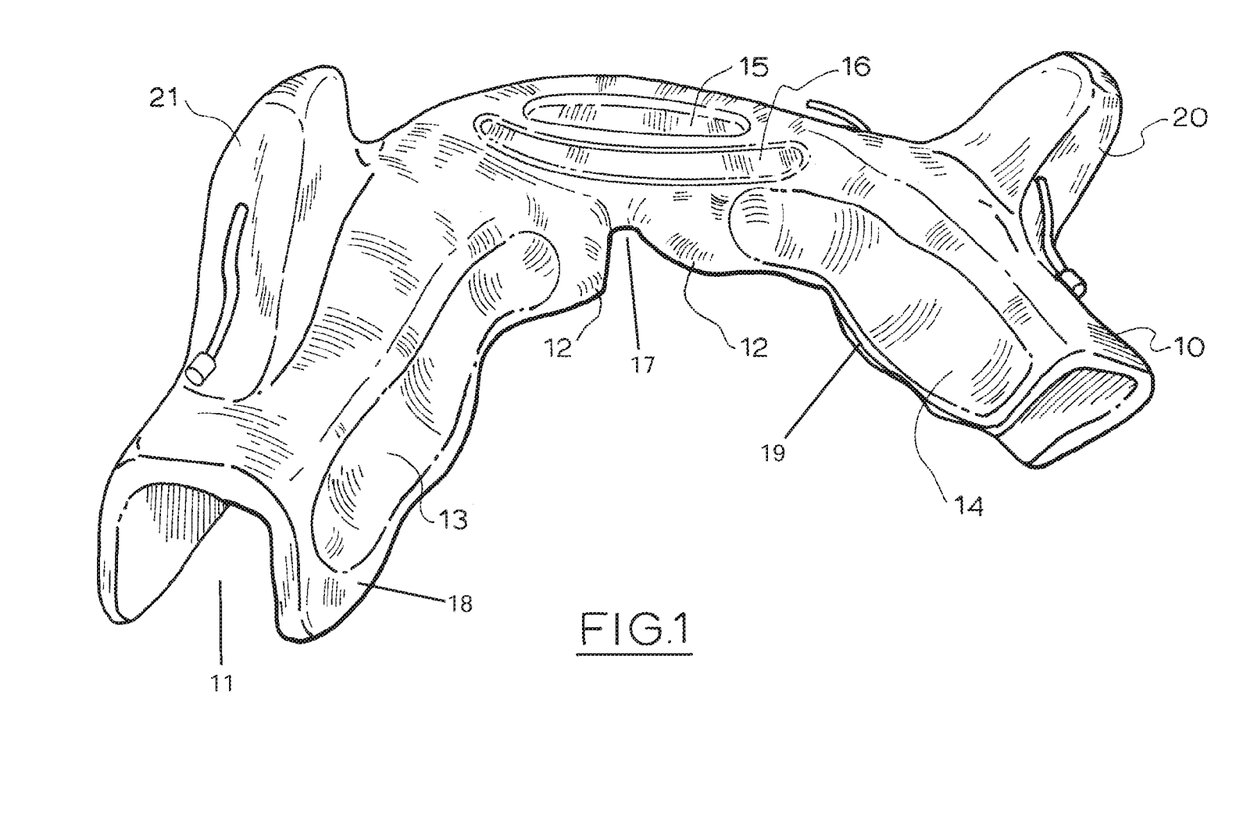
FIG. 1 is a perspective view of one implementation of the present invention.

FIG. 1 illustrates device 10 according to one aspect of the present invention. The device is based around a generally conventional splint adapted to cover the lower teeth, which are received within passage 11. Tongue support 12 projects from the front of the splint into the opening within the arc of the teeth, onto the lower palate. It includes a groove or recess 17 into which the lingual frenum of the tongue can be received, so as to maximise the ability of the tongue to project forward in the mouth.

Cavities 13 and 14 are formed within the interior walls of the device 10. These cavities provide a space within which the tongue will flow in its rested or relaxed state. Grooves 15, 16 are provided to encourage the tongue to sit forward in the mouth, using the tongue tongue reflex. Device 10 also includes lugs 21, 22 associated with operation of the device as part of an MAS device. The MAS aspects, and upper splint and associated elastics, may be entirely conventional, for example as in the devices available commercially from Somnomed Limited and other manufacturers. Accordingly, no detailed discussion of such devices will be included.

It will be appreciated that the present implementation may be a stand alone device, and not part of an MAS construction. Lugs 21, 22 are provided in this implementation as a convenience, as in the event that an MAS device is determined to be clinically appropriate, a whole new lower splint is not required.

In this implementation, the interior walls 18, 19 preferably project inwardly and away from the main section of the splint, at angle of preferably 20 to 40 degrees. Cavities 13, 14 are provided within the walls 18, 19. Cavities 13, 14 in a preferred form should enclose a space which is as large as possible, within the constraints of comfort, function and structure.

Figure 2:
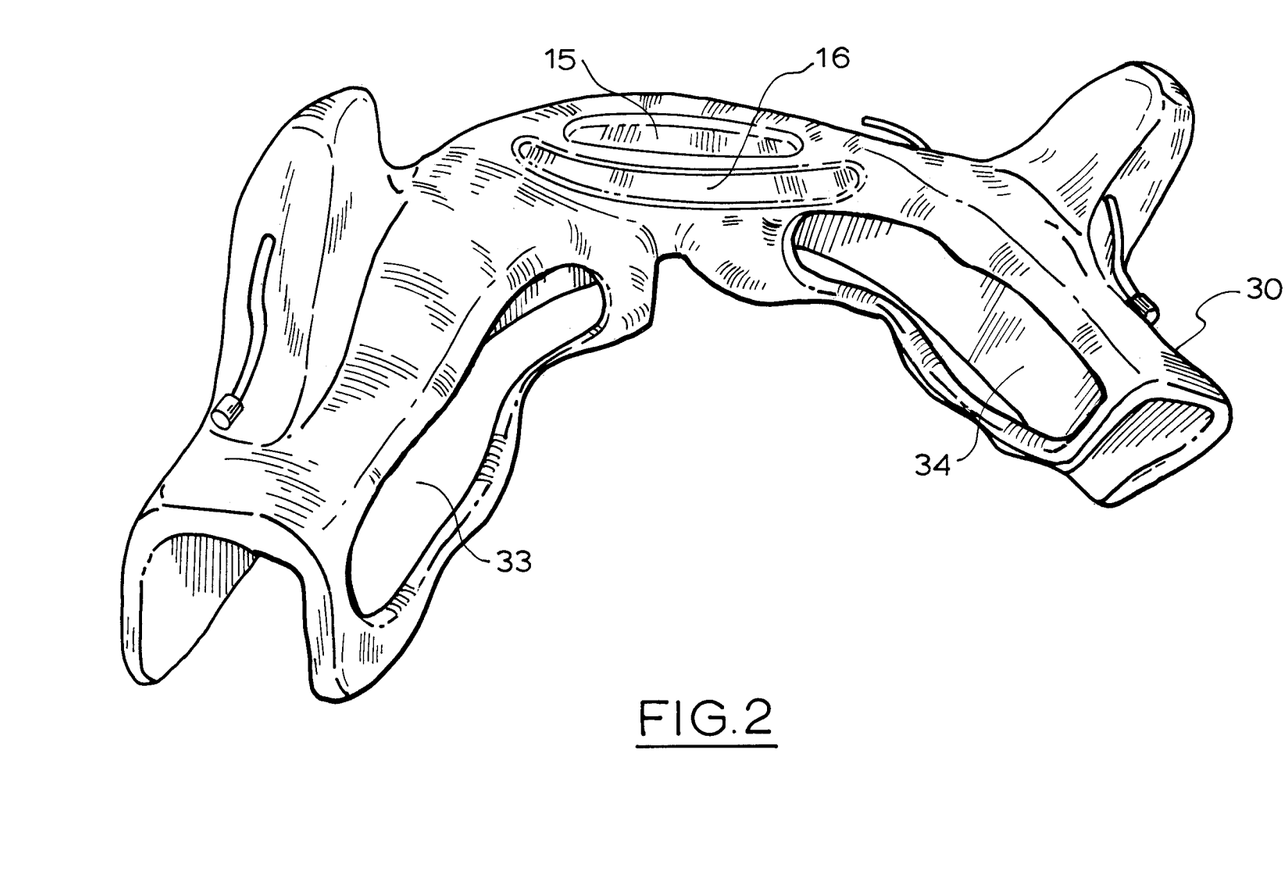
FIG. 2 is a perspective view of a second implementation of the present invention.

FIG. 2 illustrates an alternative implementation of the present invention. Device 30 includes openings 33, 34 extending completely through the interior side wall of the device. These operatively produce an opening into which the tongue may flow in a relaxed state, similar in principle to the device of FIG. 1. Other features of FIG. 2 are similar to FIG. 1.

Alternative devices similar to FIG. 1 or FIG. 2 may include a projection onto the floor of the mouth, with a cavity formed therein. Thus, the cavity need not be formed in the side walls generally parallel to the gums, but may be formed in a more vertical way, so that the cavity is generally or roughly parallel to the floor of the mouth.

Figure 3A:
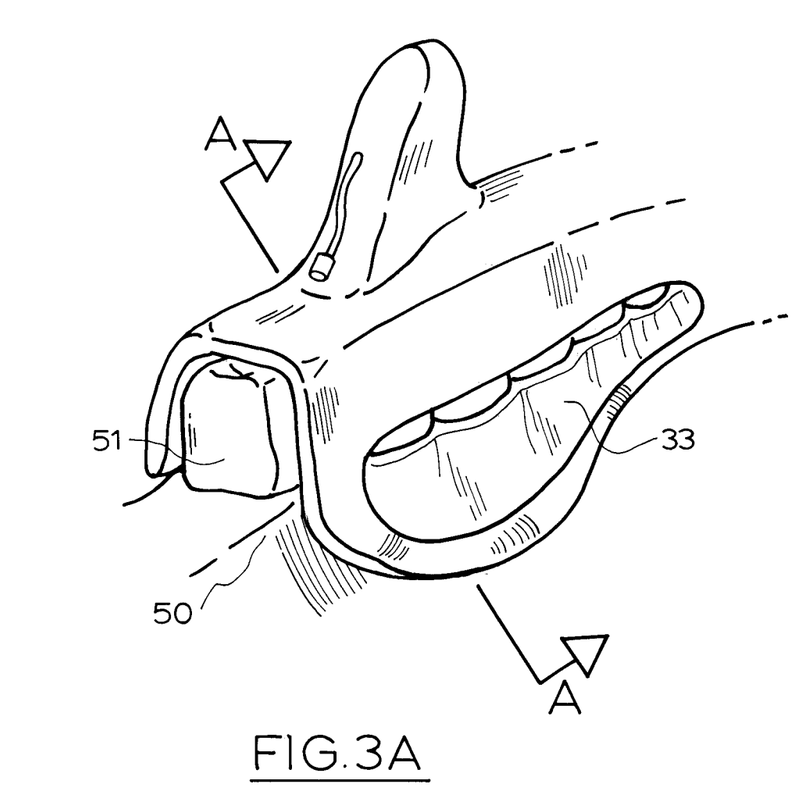
FIG. 3A is a detailed view of part of the device of FIG. 2.
Figure 3B:
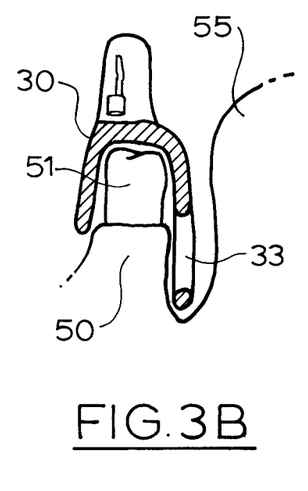
FIG. 3B is a view, partly in section, along line A-A in FIG. 3A.

FIGS. 3A and 3B illustrates a small portion of the device of FIG. 2, with a notional teeth 51 and gums 50 to better illustrate the principle of the implementation. It will be appreciated that the device and oral anatomy shown are intended schematically, and not to be anatomically or precisely accurate.

It can be seen that teeth, generally 51, are within the device 30, as is part of the associated gum 50. The openings 33, 34 extend fully through the device onto the gum 50. As can be seen in FIG. 3B, which is a section along line A-A, the cavities 33, 34 extend from at or slightly above the gum line, to near the base of the gums, and along a substantial part of the length of the teeth, corresponding to the tongue position desired.

Figure 4:
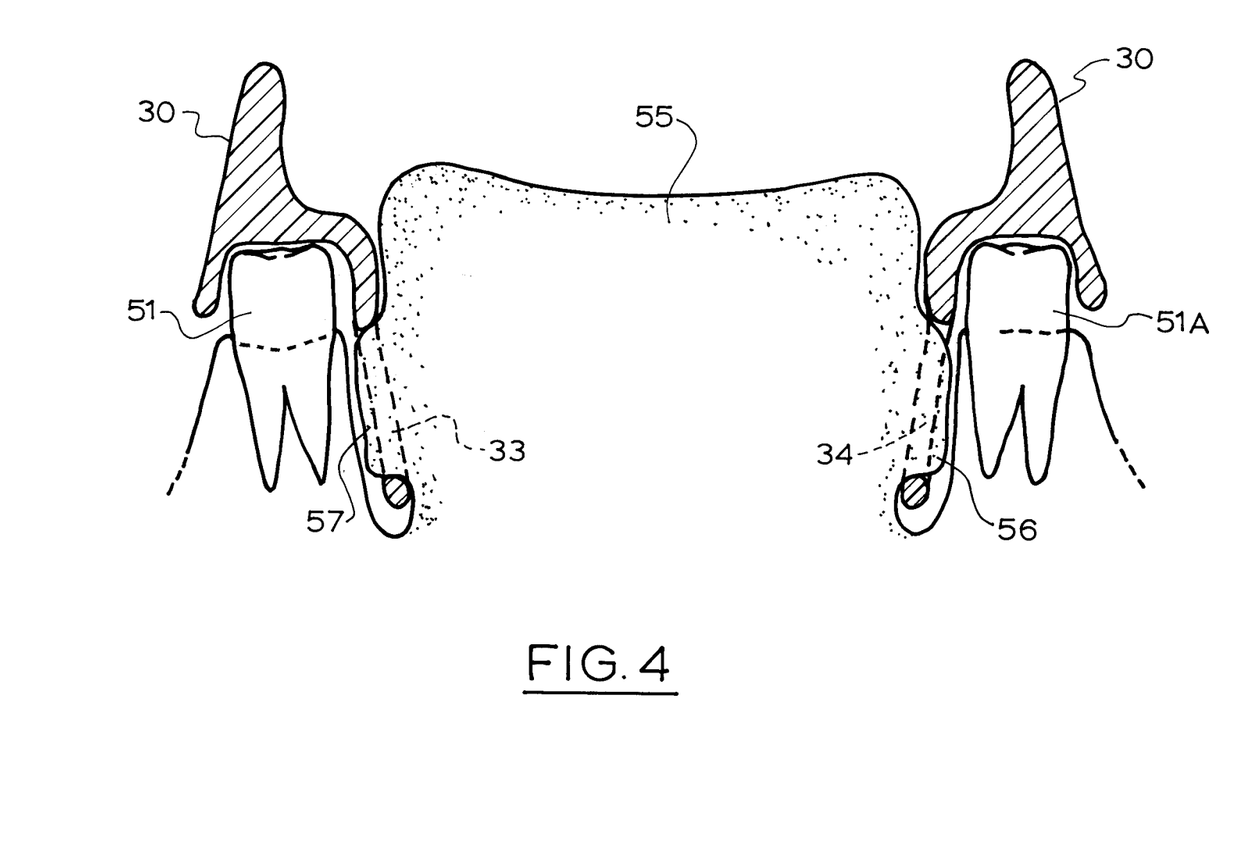
FIG. 4 is a view showing the tongue, teeth and a device according to FIG. 2.

FIG. 4 is a view, partly in section, from the rear of the mouth, particularly to illustrate the position of the tongue in the operative condition, when the tongue is relaxed and the user is asleep. The device 30 can be seen, together with teeth 51, 51A and tongue 55. The sides of the tongue relax and conform of their own accord into the cavities 33, 34, with sections of tongue 56, 57 projecting into the cavities on each side.

This implementation provides a passively actuated, natural tongue resting position, in which the TFA effect retains the tongue in the desired, forward position between the teeth, without any need for an active restraint. The tongue may be consciously withdrawn, or moved as part of a reflex action such as a sneeze or yawning, without any risk of damage to the tongue.

Trials have indicated that this is effective for many patients to retain the tongue in a more suitable position during sleep, and improve or eliminate their sleep apnoea.

Figure 5:
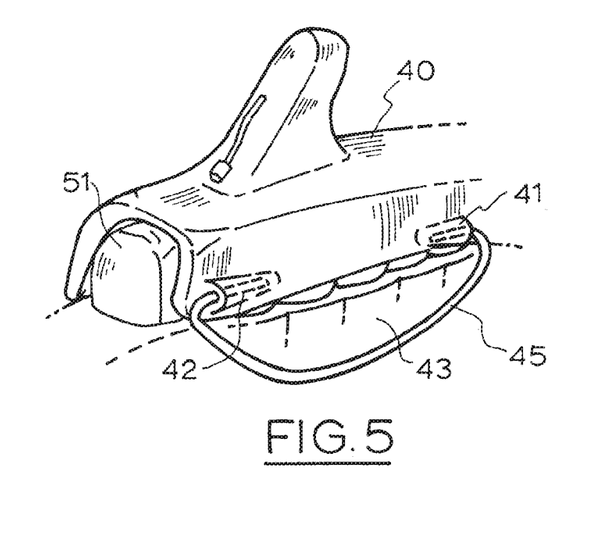
FIG. 5 is a perspective view of part of a device according to a third implementation.
Figure 6:
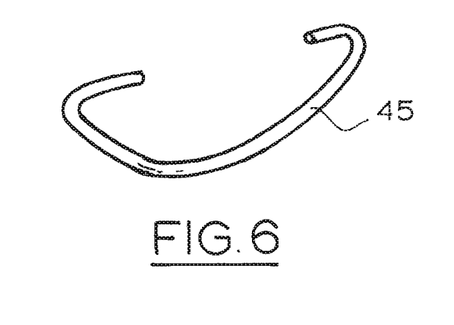
FIG. 6 is a detailed view of the extension component of FIG. 5.

FIG. 5 illustrates an alternative implementation, in which a wire extension 45 is attached to the side of the splint 40. This is retained by recesses 42, 41 and the tension in the extension 45. This forms a similar cavity to those in other implementations, bounded by the device 40, extension 45 and the teeth 51 and gums 50. The wire extension 45 serves in effect to frame the recess. FIG. 6 illustrates the wire extension in more detail. The wire may be, for example, stainless steel wire such as is commonly used in dental applications, or any suitable biocompatible material.

Figure 7:
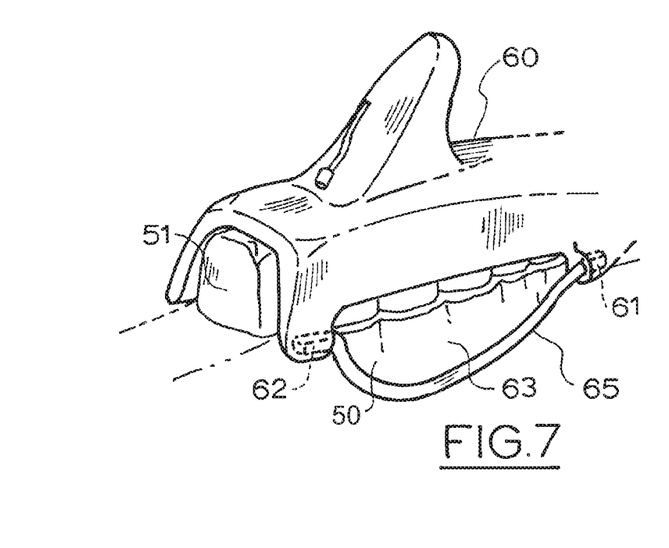
FIG. 7 is a is a perspective view of part of a device according to a fourth implementation.
Figure 8:
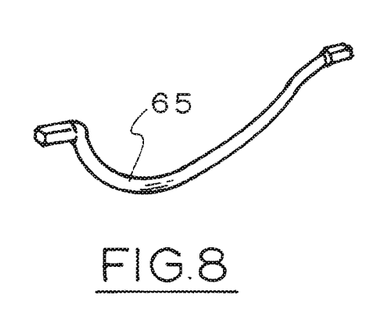
FIG. 8 is a detailed view of the extension component of FIG. 7.

FIG. 7 illustrates yet a further implementation, in which a plastic extension 65 is attached to the side of the splint 60. This is retained by recesses 62, 61 and the outward tension in the extension 65. This forms a similar cavity 63 to those in other implementations, bounded by the device 60, extension 65 and the teeth 51 and gums 50. FIG. 8 illustrates the plastic extension in more detail. The plastic section may be formed from any biocompatible material with appropriate structural properties, for example a suitable dental polymer. This component could be custom formed, or mass produced in one or more sizes for fitting to the custom splint.

It will be appreciated that a variety of attachment mechanisms could be used for the extension component, depending upon the mechanical arrangement selected and the properties of the material chosen.

Figure 9:
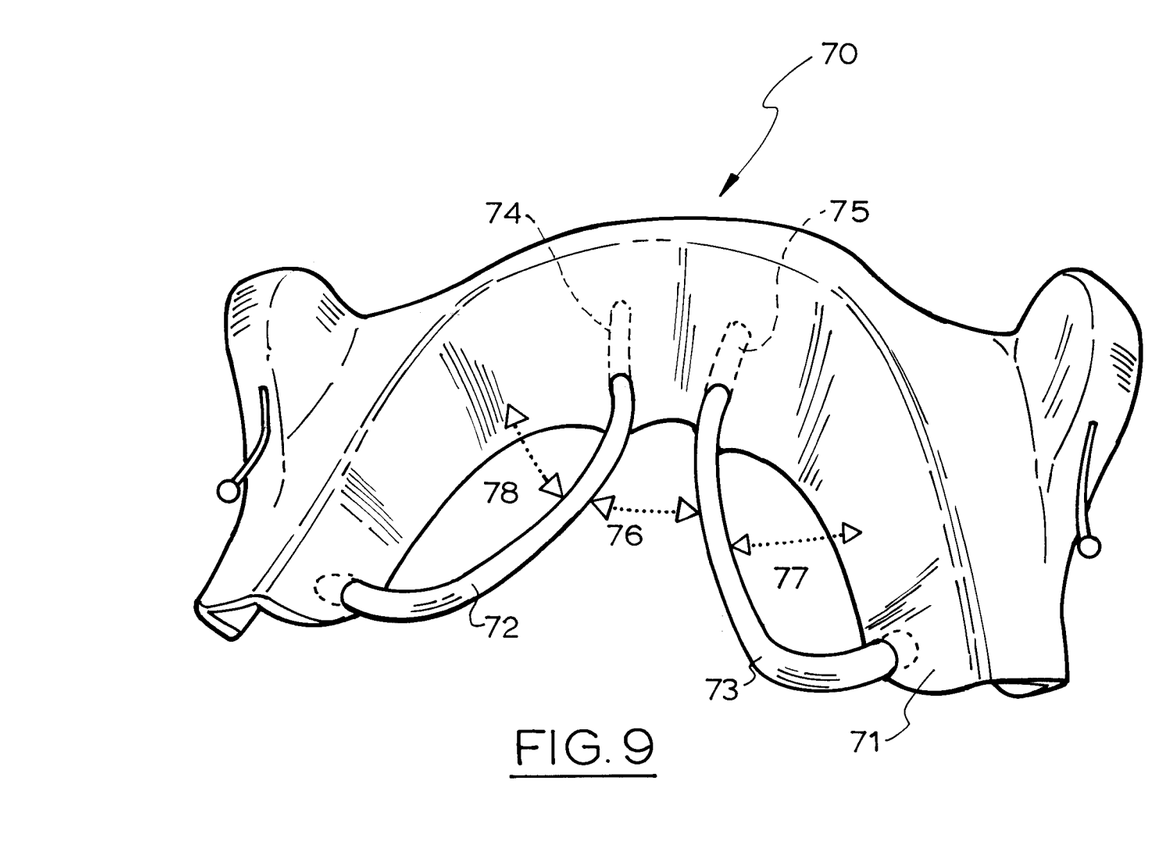
FIG. 9 is perspective view of a further implementation of the present invention.

FIG. 9 illustrates another alternative implementation according to the present invention. In this implementation, the device 70 includes metal sections 72, 73 extending from the inside face 71 of the device. In this implementation, the metal sections 72, 73 are moulded within the structure, as can be seen by dotted recesses 74, 75. The cross sectional shape of metal sections 72, 73 is preferably rounded, and most preferably tear drop shaped, with a somewhat thicker section at the bottom than the top. In this implementation, the cavities are formed by the openings within metal sections 72, 73.

It will be appreciated that in order to obtain optimal benefit, the device needs to be correctly sized for the mouth of the user. Further, the correct spacings between the components need to be present. Space 78 and space 77 need to be equal or close to equal, and the gap 76 must be neither too wide nor too narrow. This will be reflected in the reports of comfort by the user. Modification is required if the user reports discomfort, by adjusting the positions and curvature of the metal sections 72, 71.

Figure 10:
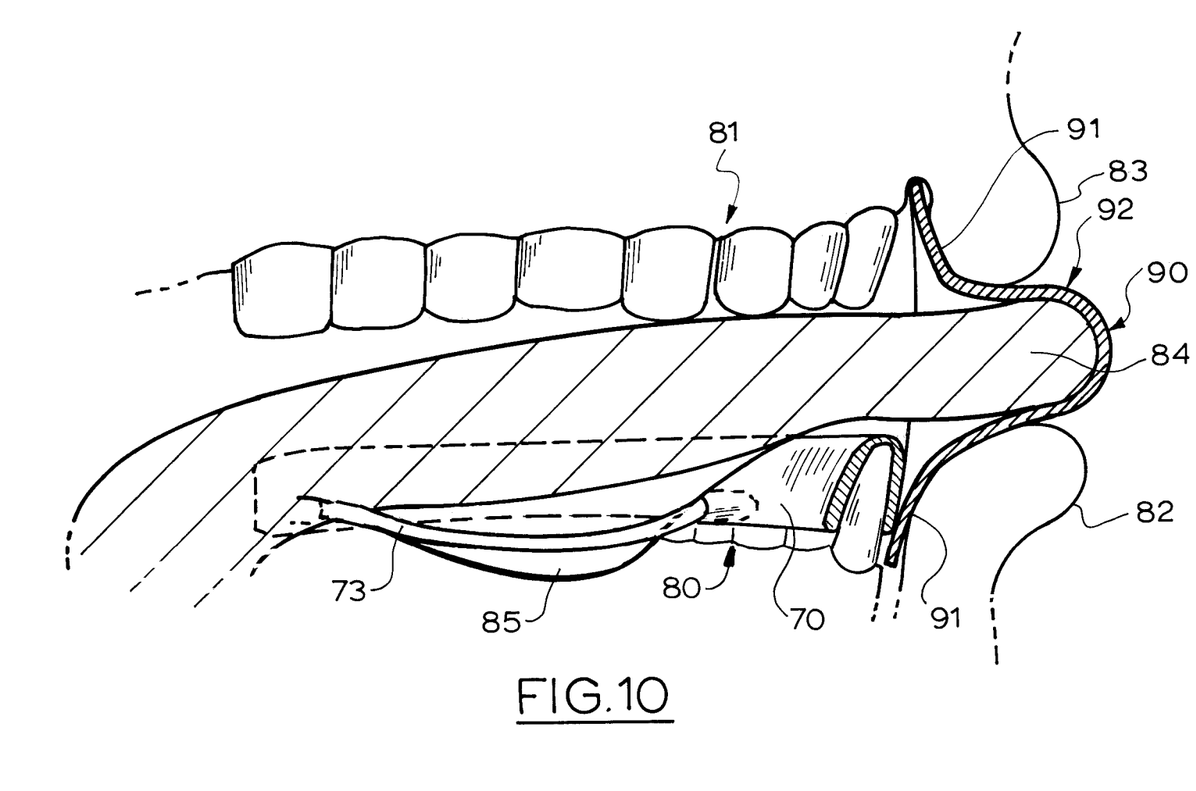
FIG. 10 illustrates, in section, the positioning of a device according to FIG. 9 with a tongue protector.

FIG. 10 is a sectional view illustrating an device similar to the device of FIG. 9 in a user's mouth. In this implementation, there is no upper splint or MAS device. Upper teeth 81 are not involved. Lower teeth 80 have a device 70 fitted. It can be seen that tongue 84 has a portion 85 projecting within the curve created by metal section 73.

In some patients, particularly those with very large tongues (macroglossia), trials have indicated that an additional component is of assistance. For some such patients, moving the tongue merely up to the inside of the lips does not provide sufficient forward movement of the tongue to adequate open the airway. However if the tongue simply protrudes from the mouth, this creates an issue of the tongue drying out and becoming a source of discomfort.

In this instance, a small, thin flexible protector may be provided which fits inside the lips and into which the tongue is inserted. The tongue is thereby protected from drying out, and the cap is retained by a abutting the lips, with a closed part protruding further. This is particularly applicable with a simple lower splint, and no MAS device.

In the implementation of FIG. 10, a tongue protector 90 is also provided. This allows for the user's tongue 84 to project out of the mouth, past teeth 81 and lips 83, 82. The protector has bubble section 92 projecting out of the mouth, and a flange 91 extending around the periphery of the protector 90, which serves to locate and retain the protector inside the mouth of the user.

Figure 11:
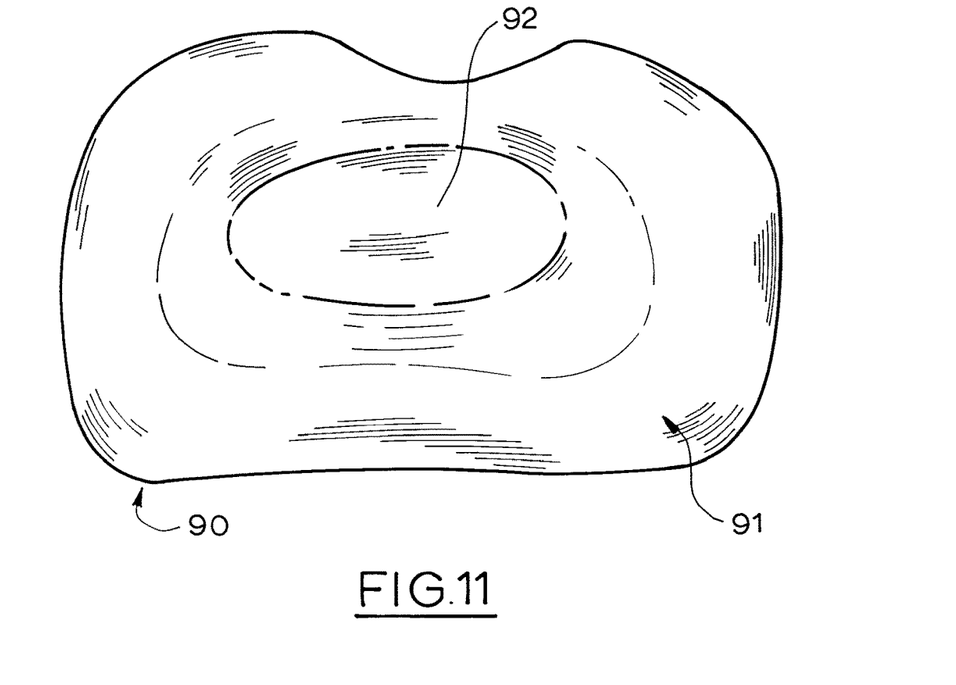
FIGS. 11 and 12 are top and perspective views of an tongue protector according to an aspect of the present invention.
Figure 12:
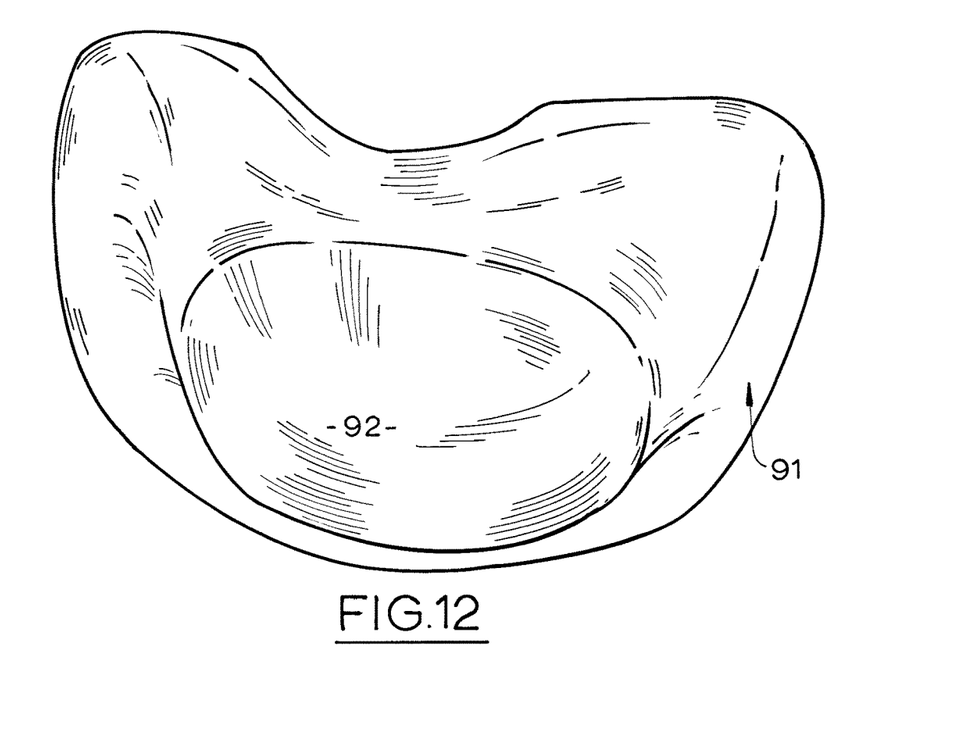

FIGS. 11 and 12 illustrate the protector in more detail. It will be appreciated that protector 90 may be formed in a variety of shapes, and that this is merely a suitable example. The protector may be formed from any suitable material, for example a polymer or silicone material. It must be somewhat flexible, but retain sufficient rigidity, especially around the flange, in order to be effectively retained in use, particularly noting that the user is intended to be asleep during use.

It is emphasises that the tongue protector does not exert any hold on the tongue. It is not intended to retain the tongue, by suction or narrowing, as the retention is accomplished by the cavities in the lower splint.

From the examples, it will be apparent that the present invention may be implemented in various ways. Whilst recognising that there are of course other possible implementations, below we will discuss several specific implementations.

In one version, the present invention can be added to an MAS device, without providing a tongue tip space in the MAS device. This will leave the tongue positioned at rest behind the teeth. In this implementation, the MAS device operates in a conventional way, but its operation is enhanced by the cavities reducing the likelihood of the tongue sagging backwards, particularly in supine sleep. This is beneficial, for example, for supine OSA in many cases where there in not a particularly large tongue, or obesity issues.

In a second application, the present invention may be added to an MAS device, with a tongue tip space, so that the tongue projects at rest past the teeth but inside the lips.

In a third application, the present invention may be applied to an MAS device, with the addition of the tongue protector. In this case, the tongue will project past the lips into the protector.

In a fourth application, the present invention may be applied to a lower splint only, with the addition of a tongue protector. This is particularly useful for cases in which mandibular advancement is contra-indicated, such for patients with jas joint issues. It is also useful where persistent snoring cannot be resolved by other means. So long at the nasal airway is patent, this is effective as the tongue protector prevents breathing through the mouth, and snoring noises are not generally present with nasal breathing. This has application, for example, where there is more tongue crowding or obstruction issues, Down Syndrome, or macroglossia.

Although the present invention is preferably implemented with a custom moulded splint, it could be implemented using a pre-formed device which is heat mouldable for example as is common for mouth guards or similar devices. For example, a variety of preformed shapes could be used. Other moulding or manufacturing processes could be used. While it is preferred, it is not essential that the device cover all the teeth, what is required is that an adequate structure is provided to provide the cavity and other structures which are provided to engage the tongue.

The cavity may be provided by any suitable structure, formed from any suitable material. For example, this may be a biocompatiable metal (e.g. titanium or stainless steel), biocompatible plastic (e.g. polycarbonate) or any other suitable material. The term cavity is to be understood in the broadest sense, and may include a opening partly or fully through the device, or a space defined by a peripheral frame or structure. The shape may be any suitable shape which achieves the desired function, of allowing the resting tongue to flow in and around the cavity and retain the tongue by virtue of the TFA effect. Preferably, the shape is selected to maximise tongue retention. The same criteria apply to the positioning of the cavity. In some implementations, it is foreseen there may be multiple cavities.

However, it is equally important that the retention be such that the tongue may be rapidly withdrawn if required. The structures defining the cavities preferably have cross sectional shapes which minimise tongue irritation, yet assist with tongue retention. In particular, the splints would be formed so that at the rear there is a minimal labial flange thickness.

It will be appreciated that there are many other ways in which a cavity or recess can be provided along the gum wall, or adjacent thereto, or along the floor of the mouth, for the tongue to rest within. For example, the shape of the cavity may be more complex, or could be discontinuous. The edges of the cavity could in relatively tapered, or less so, or vary in this along the edge. The key requirement is that operatively the relaxed tongue rests adjacent to and moves to an extent into the cavity. Any suitable shape of cavity or similar structure which provides an opening and which is operative to retain the relaxed tongue may be used to implement the present invention.

The precise shape and dimensions of the cavity or recess are subject to both the specific anatomy of the proposed user, and the constraints of the selected design. Preferably, the recess is several millimetres deep. The extensions are preferably angled inwardly, at an angle of between about 20 degrees and about 40 degrees. The tongue supporting extensions (or other structures), in a preferred form, should extend from approximately the position of the canine teeth, to the posterior molar region, generally the second molar.

In one form, the wire or plastic extensions described above could be pro-formed to specific sizes, or a variety of sizes could be available and fitted for comfort by the practitioner. In another form, the extensions (particularly in wire) could be custom modified and fitted to each user. Similar principles apply to the formed cavity or opening alternatives. It will be appreciated that there are many ways in which devices can be manufactured.

In preferred forms, as shown in FIGS. 5 and 7, pre-formed connection points are provided for the extension, to provide a more consistent device and simplify fitting and manufacture.

The walls 18, 19 in which the cavities 13, 14 are provided preferably project inwardly and away from the splint, at angle of preferably 20 to 40 degrees. The cavity, or other structure are will be described below, should enclose a space which is as large as possible, within the constraints of comfort, function and structure. It will be understood that there may need to be an adjustment to the size and shape of the cavities in order to meet the required level of comfort for the user, on a trial and error basis.

The process of fitting a device to a user according to the preferred implementation is as follows. A dentist takes a bottom mouth impression, and then a bite record which registers the correct vertical opening of the jaw. The dental laboratory then constructs a standard bottom splint, according to the bite record and impression provided by the dentist. In the case that an extension type system is used, the laboratory includes the attachment recesses for such extensions. In some implementations, the wire may be inserted into the splint.

In implementations with a recess or opening, then this is created from the custom moulded device by the technician, either in a standard position or one specified by the dentist.

At the time of fitting, the dentist will insert the extension devices, and ensure that they are the correct size to optimise the retention effect.

In the event that an MAS device is to be provided, incorporating the features of the present invention in the lower splint, then reference should be had to the details in the prior application, incorporated above by reference. Specifically, it is important to provide a tongue tip space, as described in that disclosure, between the upper and lower splints, so that the tongue is able to move as far forward as possible in the mouth. If there is no room for the tongue to move as far forward as possible, for example between or immediately behind the lips, then the optimum effect cannot be obtained from the present invention.

It is considered that in a device according to the present invention, the provision of structures to stimulate the tongue-tongue reflex and thereby encourage the tongue to project forward are less important than in the implementations described in the prior application. However, it is preferred to provide such structures on the upper and/or lower splint, in and around the tongue tip space. Such grooves, bubbles and textures may assist the tongue by providing a landmark for location of the tongue.

The invention claimed is:

1. An oral device to operatively enhance the operation of the airway of a sleeping user, the device comprising a carrier adapted to be positioned over at least some of the lower teeth of the user and having an interior projection over at least part of the gums of a user, wherein the projection defines a pair of opposed cavities, the cavities being shaped and operatively adapted so that in the sleeping user, the tongue will passively project into and engage the cavities and thereby retain the tongue, wherein the cavities are defined by one or more of a recess in the projection, an opening in the projection, or by the projection comprising a frame extending inwardly toward the tongue from the projection, and wherein the frame is formed as an open structure without an interior enclosure.

2. An oral device according to claim 1, wherein the device comprises mechanical projections to allow connection of the carrier to an upper splint, so that the carrier is adapted to form part of a mandibular advancement device.

3. An oral device according to claim 2, wherein the device further comprises an upper splint, adapted to be resiliently connected to the carrier, so as to provide a mandibular advancement device.

4. An oral device according to a claim 1, further comprising a tongue support located on the device so that operatively the tongue is positioned forward in the mouth, the tongue support comprising a set of surface features and textures, such that when the user is asleep, the tongue of the user will tend to locate on the support and thereby locate forward in the mouth.

5. An oral device according to claim 4, wherein the tongue support comprises a rearward facing recess into which the lingual frenum of the user is operatively received, so that the tongue may rest further forward in the mouth and be further supported along its length from below.

6. An oral device according to claim 1, wherein the projection comprises a frame extending inwardly toward the tongue from the projection, and the frame is formed partly or wholly from wire.

7. The oral device according to claim 1, wherein the interior projection is adapted to project downward within the mouth over at least part of the gums of a user, and the cavities are adapted to open sideways within the mouth such that the sides of the tongue of the user will passively project into and engage the cavities and thereby retain the tongue.

8. An oral device to operatively enhance the operation of the airway of a sleeping user, the device comprising a carrier adapted to be positioned over at least some of the lower teeth of the user and having an interior projection over at least part of the gums of a user, wherein the projection defines a pair of opposed cavities, the cavities being shaped and operatively adapted so that in the sleeping user, the tongue will passively project into and engage the cavities and thereby retain the tongue, wherein the device comprises mechanical projections to allow connection of the carrier to an upper splint, so that the carrier is adapted to form part of a mandibular advancement device.

9. An oral device according to claim 8, wherein the cavities are defined by one or more of a recess in the projection, an opening in the projection, or by the projection comprising a frame extending inwardly toward the tongue from the projection.

10. An oral device according to claim 9, wherein the projection comprises a frame extending inwardly toward the tongue from the projection, and the frame is formed as an open structure without an interior enclosure.

11. An oral device according to a claim 8, further comprising a tongue support located on the device so that operatively the tongue is positioned forward in the mouth, the tongue support comprising a set of surface features and textures, such that when the user is asleep, the tongue of the user will tend to locate on the support and thereby locate forward in the mouth.

12. An oral device according to claim 11, wherein the tongue support comprises a rearward facing recess into which the lingual frenum of the user is operatively received, so that the tongue may rest further forward in the mouth and be further supported along its length from below.

13. An oral device according to claim 8, wherein the device further comprises an upper splint, adapted to be resiliently connected to the carrier, so as to provide a mandibular advancement device.

14. The oral device according to claim 8, wherein the interior projection is adapted to project downward within the mouth over at least part of the gums of a user, and the cavities are adapted to open sideways within the mouth such that the sides of the tongue of the user will passively project into and engage the cavities and thereby retain the tongue.

15. An oral device to operatively enhance the operation of the airway of a sleeping user, the device comprising a carrier adapted to be positioned over at least some of the lower teeth of the user and having an interior projection over at least part of the gums of a user, wherein the projection defines a pair of opposed cavities, the cavities being shaped and operatively adapted so that in the sleeping user, the tongue will passively project into and engage the cavities and thereby retain the tongue, further comprising a tongue support located on the device so that operatively the tongue is positioned forward in the mouth, the tongue support comprising a set of surface features and textures, such that when the user is asleep, the tongue of the user will tend to locate on the support and thereby locate forward in the mouth.

16. An oral device according to claim 15, wherein the cavities are defined by one or more of a recess in the projection, an opening in the projection, or by the projection comprising a frame extending inwardly toward the tongue from the projection.

17. An oral device according to claim 16, wherein the projection comprises a frame extending inwardly toward the tongue from the projection, and the frame is formed as an open structure without an interior enclosure.

18. The oral device according to claim 15, wherein the interior projection is adapted to project downward within the mouth over at least part of the gums of a user, and the cavities are adapted to open sideways within the mouth such that the sides of the tongue of the user will passively project into and engage the cavities and thereby retain the tongue.

19. A method of forming an oral device for operatively enhancing the operation of a sleeping user's airway, the method comprising the steps of forming a device adapted to be positioned over at least some of the lower teeth of the user, and forming an interior projection over at least part of the gums of a user, the projection defining a pair of opposed cavities, the cavities being shaped and operatively adapted so that the tongue of the sleeping user will passively project into and engage the cavities, wherein the cavities are defined by one or more of a recess in the projection, an opening in the projection, or by the projection comprising a frame extending inwardly toward the tongue from the projection, and wherein the frame is formed as an open structure without an interior enclosure.

20. A method according to claim 19, wherein the frame is formed partly or wholly from wire.

* * * * *